US007842058B2

(12) United States Patent
Simpson et al.

(10) Patent No.: US 7,842,058 B2
(45) Date of Patent: Nov. 30, 2010

(54) MANIPULATION AND CUTTING SYSTEM AND METHOD

(75) Inventors: Philip J. Simpson, Escondido, CA (US); David G. Matsuura, Encinitas, CA (US); Walter Dean Gillespie, San Diego, CA (US)

(73) Assignee: Flex Partners, Inc., Encinitas, CA (US)

(*) Notice: Subject to any disclaimer, the term of this patent is extended or adjusted under 35 U.S.C. 154(b) by 484 days.

(21) Appl. No.: 10/771,093

(22) Filed: Feb. 2, 2004

(65) Prior Publication Data
US 2007/0167966 A1    Jul. 19, 2007

Related U.S. Application Data

(60) Provisional application No. 60/444,326, filed on Jan. 31, 2003.

(51) Int. Cl.
*A61B 17/32* (2006.01)
(52) U.S. Cl. ................................... 606/170
(58) Field of Classification Search ......... 606/167–180, 606/131, 132, 159, 163–165, 79–85; 83/491, 83/596, 603; 30/93, 102, 164.95, 292, 306–307, 30/319, 365, 389
See application file for complete search history.

(56) References Cited

U.S. PATENT DOCUMENTS

| 3,605,837 | A | * | 9/1971 | Lambert et al. | 83/73 |
| 3,797,343 | A | * | 3/1974 | Miller et al. | 83/80 |
| 4,950,277 | A | * | 8/1990 | Farr | 606/159 |
| 5,098,392 | A |  | 3/1992 | Fleischhacker et al. |  |
| 5,101,564 | A |  | 4/1992 | Melter | 30/319 |
| 5,221,263 | A |  | 6/1993 | Sinko et al. |  |
| 5,429,598 | A |  | 7/1995 | Waxman et al. |  |
| 5,468,247 | A |  | 11/1995 | Matthai et al. | 606/178 |
| 5,591,186 | A | * | 1/1997 | Wurster et al. | 606/170 |
| 5,919,203 | A |  | 7/1999 | Husted et al. |  |
| 6,451,017 | B1 | * | 9/2002 | Moutafis et al. | 606/41 |

FOREIGN PATENT DOCUMENTS

WO    WO 03/008020    1/2003

OTHER PUBLICATIONS

European Search Report issued Mar. 17, 2010 in corresponding EP 04707425.

* cited by examiner

*Primary Examiner*—Darwin P Erezo
*Assistant Examiner*—Gregory Anderson
(74) *Attorney, Agent, or Firm*—David H. Jaffer; Pillsbury Winthrop Shaw Pittman LLP

(57) ABSTRACT

A system for rapid manipulation and cutting that includes a housing, a first cutting element, and a drive mechanism adapted to be mounted at least partly within the housing and connected to the first cutting element for imparting relative motion to the first cutting element as a combination of slicing and downward forces at the portion of the first cutting element which is adapted to contact the tissue.

24 Claims, 18 Drawing Sheets

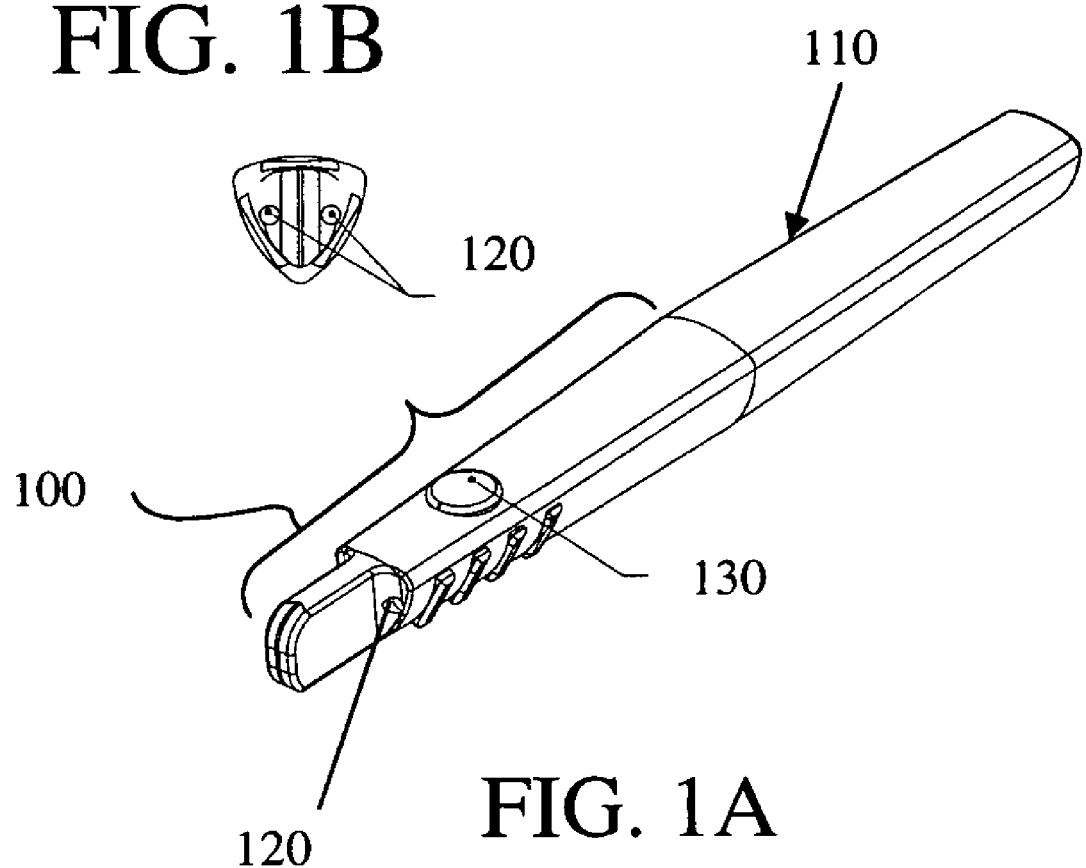

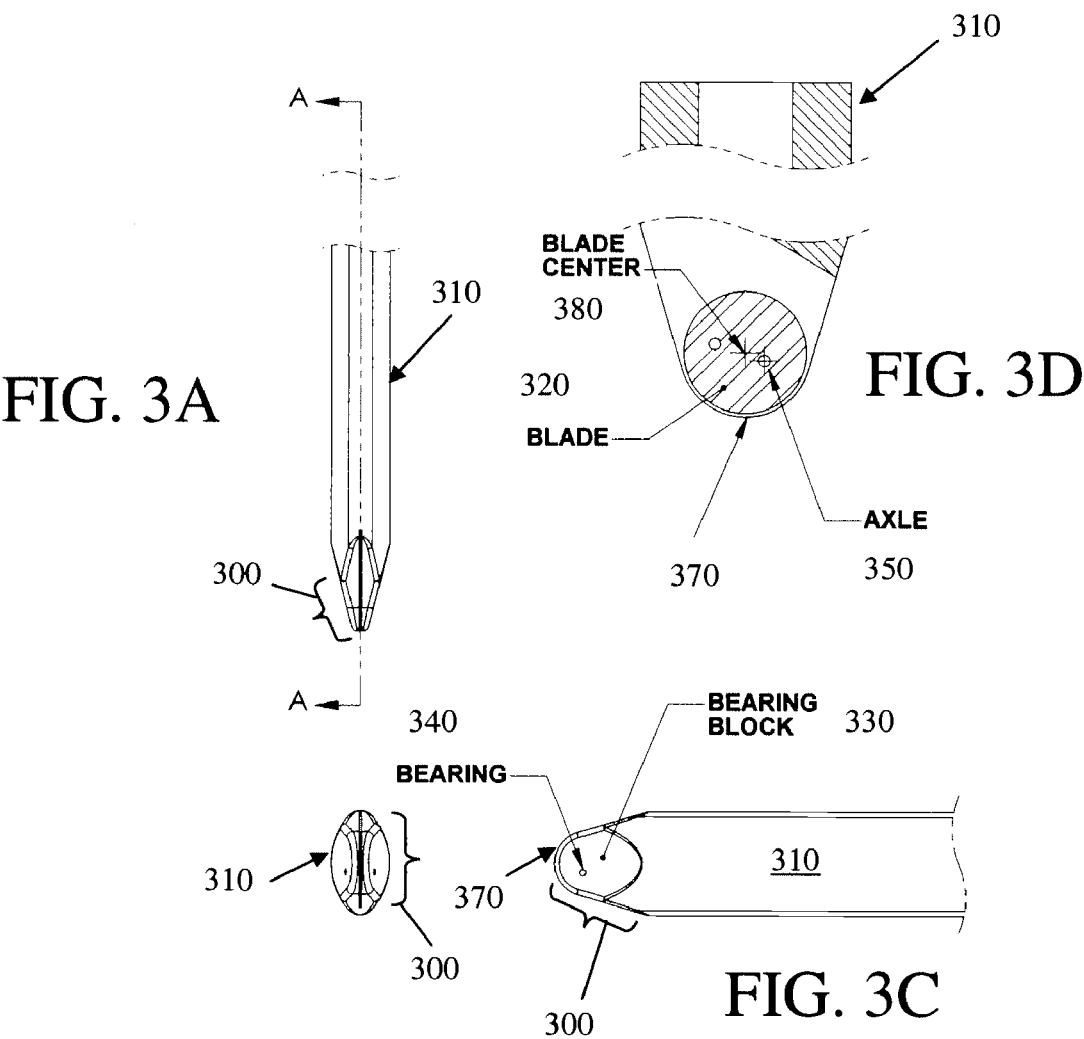

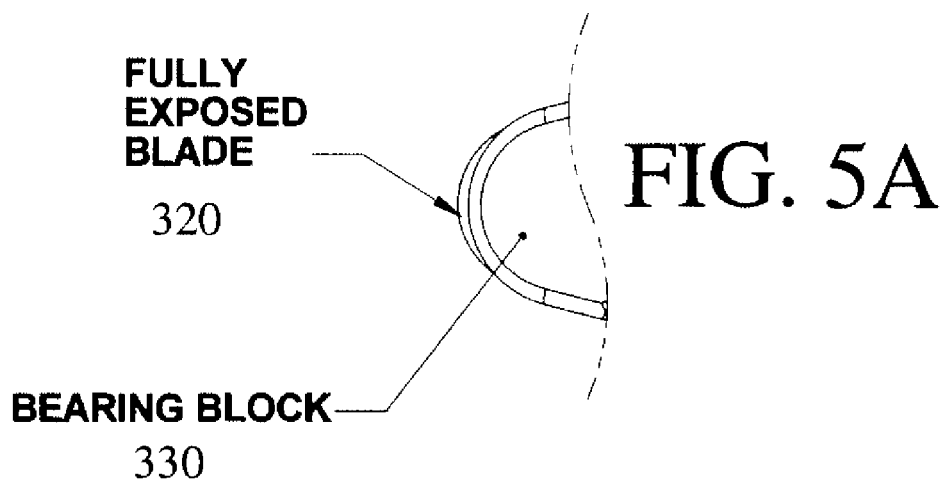
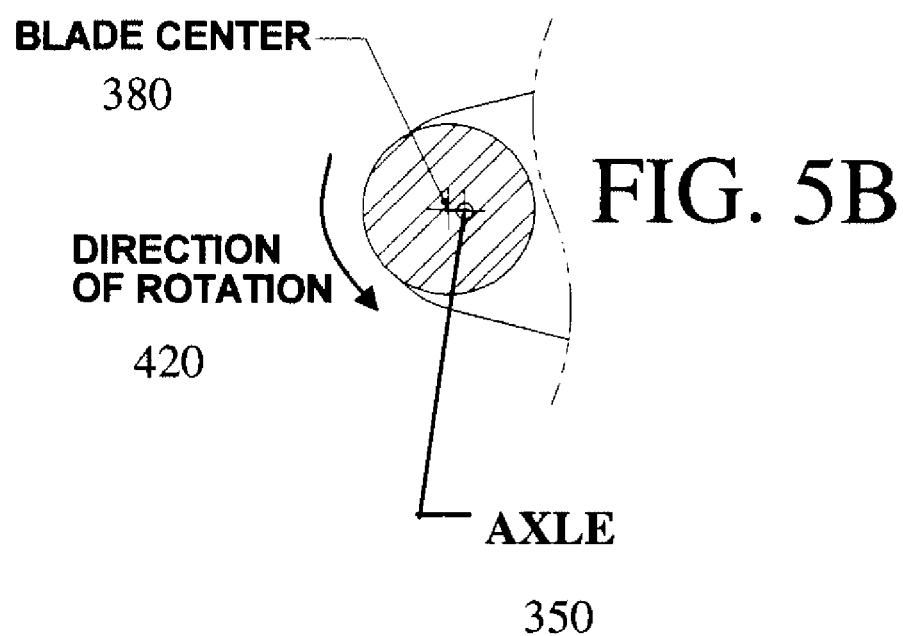

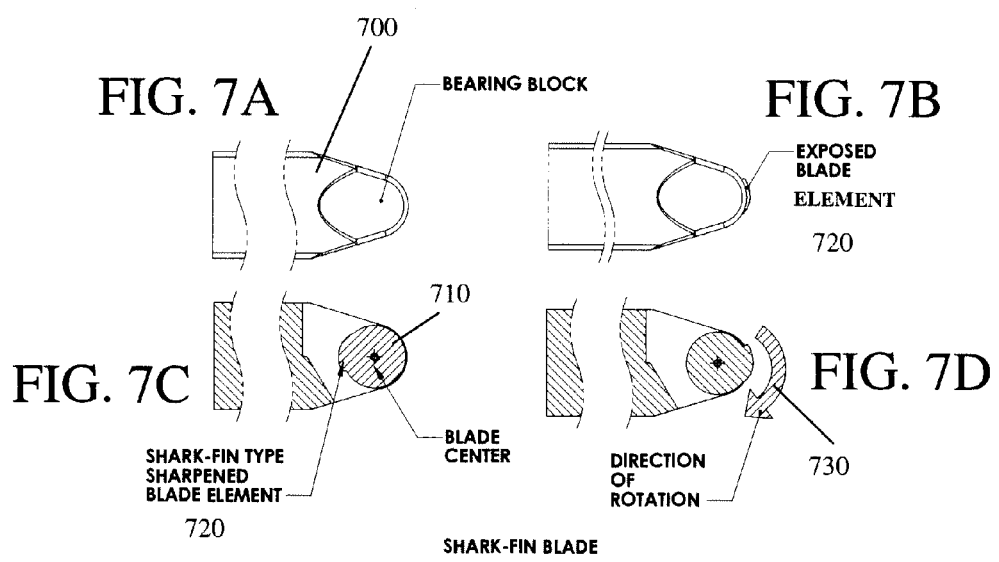

710

ELLIPTICAL BLADE

FIG. 9A
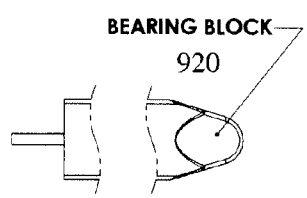
FIG. 9B
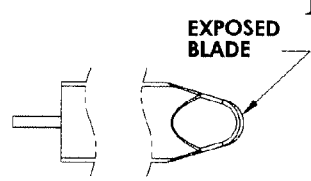
FIG. 9C
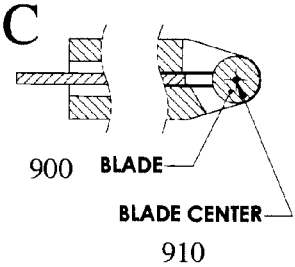
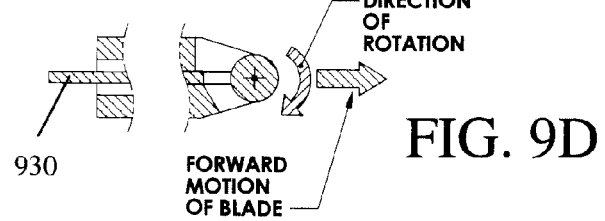
FIG. 9D
ADVANCING ROUND BLADE FIG. 10A
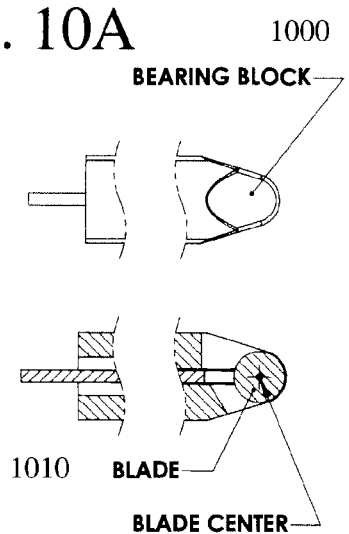
FIG. 10C
FIG. 10B
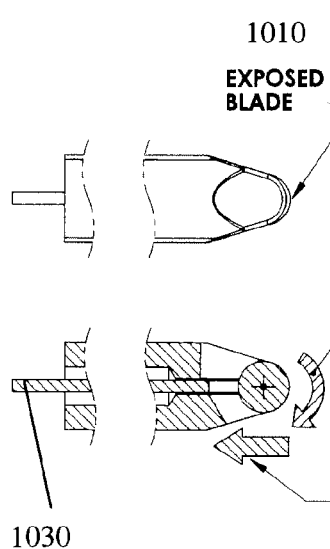
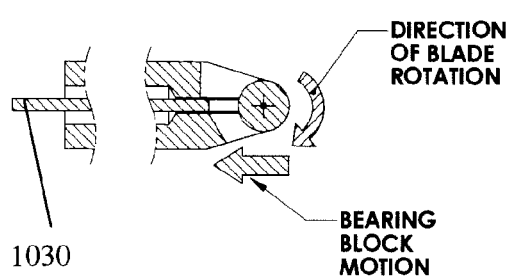
RETREATING BEARING BLOCK
FIG. 10D

FIG. 11A
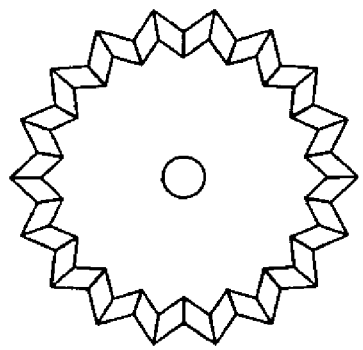
POINTS
FIG. 11B
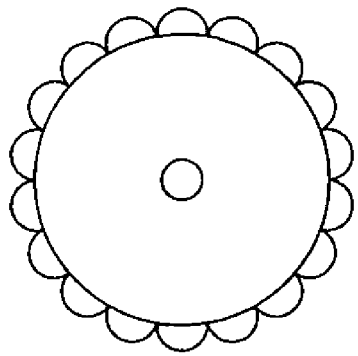
PETALS
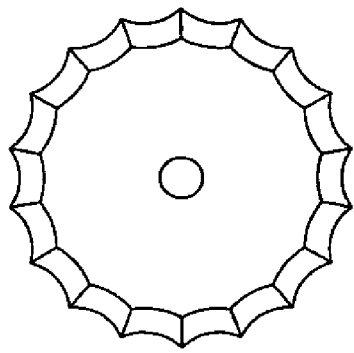
SERRATED
FIG. 11C
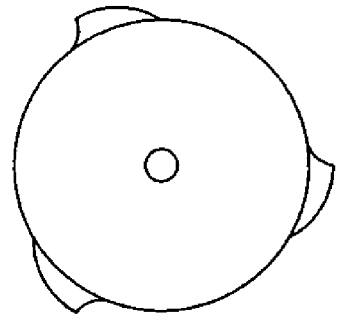
SHARK FINS
FIG. 11D

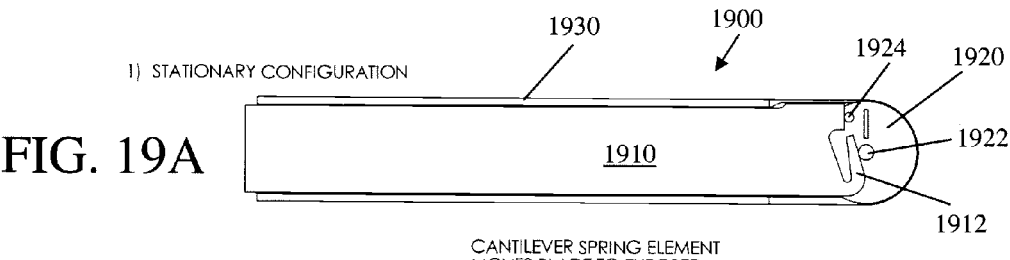

FIG. 19A  1) STATIONARY CONFIGURATION

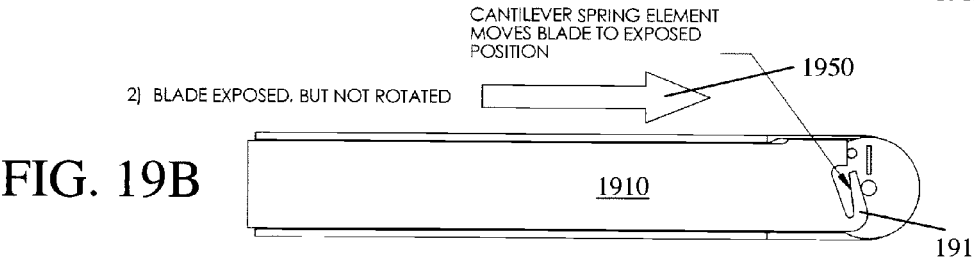

FIG. 19B  2) BLADE EXPOSED, BUT NOT ROTATED

CANTILEVER SPRING ELEMENT MOVES BLADE TO EXPOSED POSITION

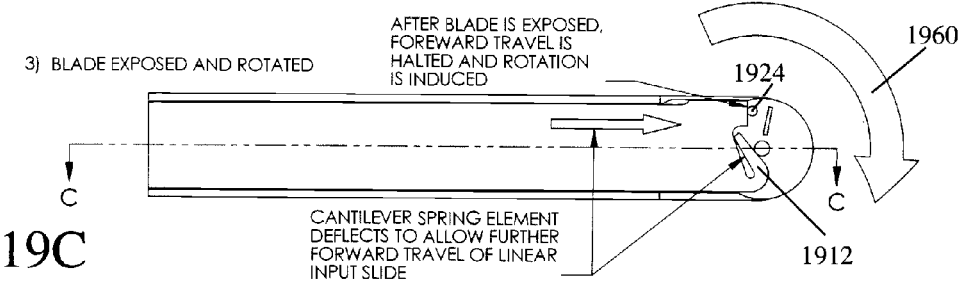

FIG. 19C  3) BLADE EXPOSED AND ROTATED

AFTER BLADE IS EXPOSED, FOREWARD TRAVEL IS HALTED AND ROTATION IS INDUCED

CANTILEVER SPRING ELEMENT DEFLECTS TO ALLOW FURTHER FORWARD TRAVEL OF LINEAR INPUT SLIDE

FIG. 19D

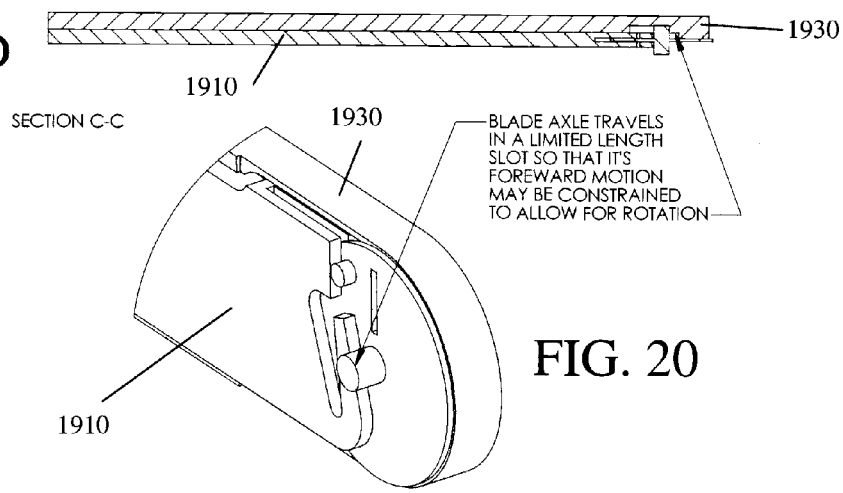

SECTION C-C

BLADE AXLE TRAVELS IN A LIMITED LENGTH SLOT SO THAT IT'S FORWARD MOTION MAY BE CONSTRAINED TO ALLOW FOR ROTATION

FIG. 20

MANIPULATION AND CUTTING SYSTEM AND METHOD

RELATED APPLICATION

This application claims the benefit of provisional U.S. Patent Application Ser. No. 60/444,326, filed Jan. 31, 2003 and having the same inventors and same title as the present application, and which is incorporated herein by reference.

FIELD OF THE INVENTION

The present inventions relate to devices and techniques for manipulation and cutting, and more particularly relate to eccentric rotary mechanisms for the cutting and manipulation and methods therefore.

BACKGROUND OF THE INVENTION

A known cutting device is the rotary slicer. Where meat is advanced into a thin blade rotating at relatively high speeds. The cutting action of this device is defined by the high slicing to chopping ratio. The resultant blade velocity vector is nearly normal to the direction of advancement. Webb, U.S. Pat. No. 5,569,285 describes a hand powered circular rotary surgical blade with a concentrically mounted cylindrical depth guard. Mueller, U.S. Pat. No. 5,507,764, describes a powered rotary scalpel method that is capable of developing a relatively high blade velocity relative to linear hand speed in the direction of cutting.

For certain clinical procedures, it is very important to make incisions to a precisely controlled pre-determined depth. Certain known devices and methods can be found that address the need to control depth of cut such as Feldman, U.S. Pat. No. 2,882,598 and Williams, U.S. Pat. No. 4,473,076, which describe a depth limiting foot or ski element used in conjunction with a scalpel. Another known method is Urban, U.S. Pat. No. 5,860,996, that discloses a blade actuating assembly, which permits selective longitudinal linear reciprocal movement of a tissue cutting blade positioned at a distal end of a trocar assembly, from a non-deployed position to a deployed position and back to a non-deployed position. The Urban device moves in a longitudinal motion only and punches into the tissue.

The known methods of tissue incision include the use of scalpels and scissors that mechanically cut the target tissue. Scalpels and scissors are useful tools when the sharp edges of the devices are clearly in view of the clinician. However, during certain procedures the sharp edge or edges may be hidden from view and prohibit the safe use of the cutting instrument. Furthermore, as the edges are hidden, it is very difficult to determine the precise depth of cut. Other methods of tissue manipulation include the dissection of different structures along natural lines by dividing or tearing the connective tissues. A blunt or sharpened obturator, such as those used with trocars, may also be used to cut and/or dissect tissue. Again, with these devices it is difficult to determine the precise depth of cut. Electrocautery devices are commonly used to surgically separate tissue. Other means of tissue manipulation include the use of energy-assisted scalpels. These devices make use of ultrasonic, laser, and radio frequency energies to assist in the manipulation of tissues. Excess energy delivered by these devices can result in collateral tissue damage, such as thermal charring and desiccation. Therefore, what is needed is a system and method for cutting that will allow precise control of the cutting edge and for rapid cutting of various materials including incision or dissection of tissues in a more controlled manner than currently exists.

SUMMARY OF THE INVENTION

The present invention provides a means for rapid cutting of various materials including incision or dissection of tissues in a more controlled manner than currently exists. As an aspect of one exemplary embodiment of the invention, a blade and blade actuation mechanism is provided that allows for simultaneous rotation and advancement of a cutting edge. In one arrangement of the invention, the system of the present invention provides an appropriate blend of slicing and downward force in order to cut efficiently. In one exemplary arrangement, at least two such motions are combined when cutting, thereby enhancing the efficiency of a blade element in at least some applications.

Another aspect of the invention, present in at least some embodiments, is to optimize the efficiency of the cutting action by providing, for a cut along a straight path, linear motion along two of the three principal axes which beneficially affect cutting performance (slicing and downward forces) and in addition provide beneficial torque about the lateral axis, while minimizing motion and torque which is not beneficial, such as linear motion along the lateral axis or torque on the principal axes. It will be appreciated that, for a straight cut, linear motion relative to the longitudinal axis of the cutting element results in a slicing cut, and linear motion relative to the vertical axis results in a chopping or plunge cut. It will also be appreciated that a slicing motion is the result of torque.

In another aspect of at least certain embodiments of the invention, a system of optimized load parameters is determined. The factors used in determining load parameters may include some or all of the: type of tissue to be incised, desired incision results including incision depth, curved or straight cutting edge, and curvilinear or straight cutting paths. The resultant optimized load parameters include, in at least certain embodiments: the resultant force vector; velocity and acceleration; and uniformity and/or consistency of load rates and velocity.

Another aspect of at least some embodiments of the invention is the flexibility to use the cutting system as a tissue manipulator for blunt dissection, or as a tissue probe. Various housings, drive mechanisms and cutting element shapes are proposed, with the application impacting the particular implementation of each of these elements in each specific implementation.

BRIEF DESCRIPTION OF THE FIGURES

FIGS. 1A-1B illustrate a cutting assembly in accordance with the present invention mounted at the distal tip of a pen-style housing, with FIG. 1B further showing a front elevational view including an illumination source.

FIGS. 3A-3D illustrate various details of a first implementation of a cutting assembly in accordance with the invention.

FIGS. 5A-5B illustrate an alternative range of motion for a cutting assembly in accordance with the invention.

FIGS. 7A-7D illustrate various details of a cutting assembly having a shark-fin style blade.

FIGS. 9A-9D illustrate various details of a cutting assembly having an advancing round blade.

FIGS. 10A-10D illustrate various details of a cutting assembly having a retreating bearing block.

FIGS. 11A-11D illustrate a few of the many possible blade shapes usable with the cutting assembly of the present invention.

FIGS. 19A-19D illustrates an implementation of a cutting assembly having a cantilever spring element.

FIG. 20 illustrates a detailed perspective view of the cutting assembly of FIGS. 19A-19D.

DETAILED DESCRIPTION OF THE INVENTION

Referring first to FIGS. 1A and 1B, a cutting assembly 100 may be mounted at the distal tip of a pen like housing 110. The cutting assembly 100 may be used for cutting various materials. As one example, not intended to be a limitation, the cutting assembly can be used to cut commercially manufactured materials, such as paper or plastic, as well as organic material, such as animal or human tissue. The cutting assembly 100 can be made in a variety of shapes, but for the sake of clarity the cutting assembly 100 is shown to emulate the shape of a hand held cutting instrument, such as a scalpel. Furthermore, for the sake of clarity, the cutting assembly will be discussed or described herein in the context of cutting or manipulating organic tissue. However, the functional elements discussed and the methods set forth can easily be applied to applications relating to cutting manufactured materials, such as Kevlar or other fabrics.

Considered in the context of cutting animal or human tissue, the cutting assembly 100 described herein requires less lateral tissue stabilization, thus allowing the user—for example, a clinician—to perform more precise curvilinear incisions. Furthermore, illumination elements, such as LED's 120, which are best seen in FIG. 1B may be added to enhance the clinician's view of the target tissue. An activation button 130 is typically provided to actuate the cutting assembly 100 as described in greater detail hereinafter. The housing 110 may also contain batteries, appropriate connectors, and/or a power switch, and may be disposable or reusable, depending on the particular implementation.

Figures 2A, 2B:
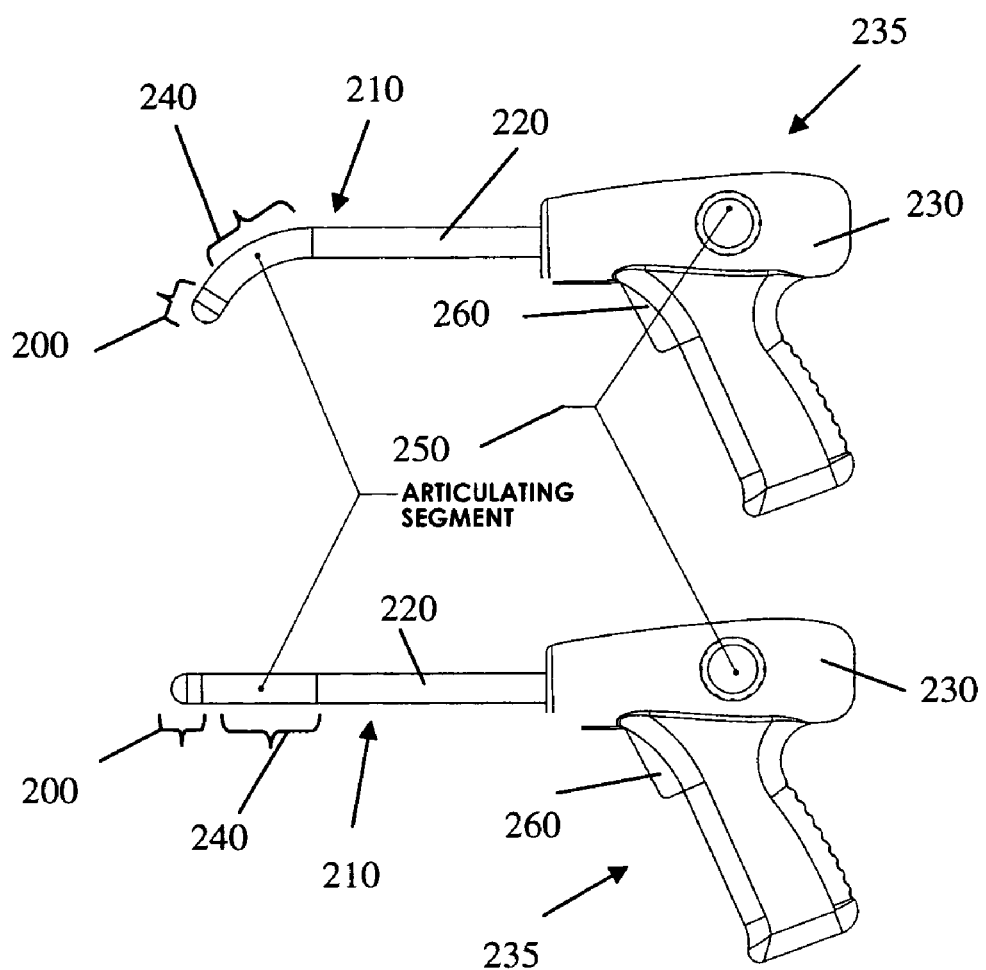
FIGS. 2A-2B illustrate a cutting assembly in accordance with the present invention mounted on a handpiece.

Referring next to FIGS. 2A and 2B, a cutting element assembly 200 in accordance with the present invention may alternatively be mounted at the distal tip 210 of an elongate cannula-like structure 220 that is connected to a hand piece 230, thus forming a tool 235 suitable for Laparoscopic surgical uses, as well as any other application in which a hand piece will simplify repositioning or operation of the cutting assembly 200. Additionally, an articulating mechanism 240 may be added proximally to the cutting element 200 to enhance user-directed positioning of the tool 235, which may in turn be adjusted by articulation control 250. A trigger or other actuator 260 is provided to actuate the cutting assembly 200. The trigger 260 could be implemented as a conventional trigger, a variable speed switch, an on/off pushbutton, or any other form of actuator. The housing could also include an internal working channel, a light, a scope or a camera, again chosen based on the particular implementation.

As a still further alternative, the cutting element assembly 200 in accordance with the present invention may be mounted at the distal tip of an elongate cannula like structure 220 and connected to robotic assembly.

Referring next to FIGS. 3A-3D, a first implementation of a cutting assembly 300 that incorporates at least some of the features of the invention can be better appreciated. FIG. 3A illustrates in top plan view the distal end of a housing 310 and the cutting assembly 300. FIG. 3B illustrates a front elevation view of the cutting assembly 300 including a rotary cutting blade 320. FIG. 3C illustrates a side elevation view of the cutting assembly 300 and the housing 310 and FIG. 3D illustrates a cut-away view showing the cutting blade 320 and the housing 310 along the line A-A in FIG. 3A. The cutting assembly 300 includes a bearing block 330 that supports a bearing 340. An axle 350 passes through an eccentric bore in the cutting blade 320 and into the bearing 340, such that the bearing block 330 provides a low friction pivot for the cutting blade 320, provides protection from the cutting blade 320 when not actuated, and limits the amount of the cutting blade 320 that is exposed when actuated during a cutting event. Furthermore, the bearing block 330 aligns the cutting blade 320 along a desired cutting path, allows cutting motions only in beneficial directions and inhibits or prevents motion in non-beneficial directions. The degree of blade eccentricity, as defined by the location of the eccentric bore in the cutting blade 320, defines the depth of cut and the ratio of slicing motion to plunging motion.

A separate external driver mechanism, discussed hereinafter in connection with FIGS. 14-18, is required to urge the blade about the pivot and to define the cutter velocity. A source of motive force, such as a motor and energy storage device, form part of the driver mechanism. The incision system of FIGS. 3A-3D operates as follows. For the sake of convenience only, a housing of the sort shown in FIG. 1 will be assumed, although the particular form of housing is not limiting. A user initiated cutting event begins by actuating an activation switch, such as the activation switch 130 of FIG. 1, which causes the driver mechanism to provide a resultant rotational movement of the cutting blade about the cutting blade pivot or axle. The cutting blade, such as the cutting blade 320 of FIGS. 3A-3D, has an eccentric bore and, hence is eccentrically mounted. Accordingly, upon rotation of the eccentrically mounted cutting blade about the pivot, the cutting edge simultaneously advances and rotates into the target tissue.

In one arrangement, the eccentrically mounted circular cutting blade is intermittently rotated at least one complete revolution as a means of cutting tissue. Many other cutting motions are possible, including reciprocating movement, partial rotation, continuous rotation, and intermittent rotation through less than a full revolution.

As shown best in FIG. 3D, in a first position, the eccentrically mounted cutting blade 320 is "parked" or rotated to a safe state where no part of the cut-ting blade 320 extends beyond a distal tip 370 of the bearing block 330 in order to protect against and prevent accidental contact with the cutting blade 320. In this position, clinicians and the patient are protected from the cutting blade 320 by the distal tip 370 of the bearing block 370. In this first position the cutting assembly 300 may be used as a tissue manipulator for blunt dissection, or as a tissue probe.

By rotating the cutting blade 320 about the axle 350, the eccentric mounting of the cutting blade 320 causes a portion of the cutting blade 320 to be exposed beyond the bearing block 330, thus allowing tissue to be cut. The exact amount of the cutting blade 320 that is exposed by such rotation is determined by the location of the eccentric bore in the cutting blade 320 relative to the blade center 380, and the extent to which the cutting blade 320 is rotated about the bearing block 330, which can be better appreciated from FIGS. 4A-4B.

Figure 4A:
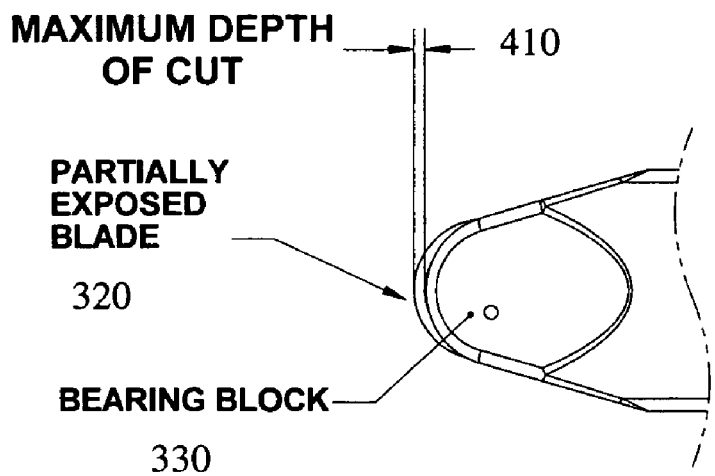
FIGS. 4A-4B illustrate the range of motion of a first implementation of a cutting assembly in accordance with the invention.
Figure 4B:
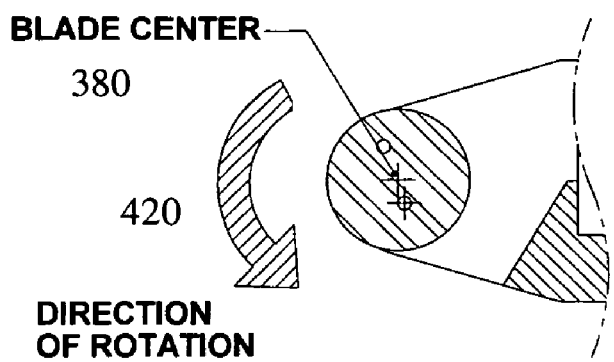

FIG. 4A shows a side elevation view of the bearing block 330 and the cutting blade 320, and FIG. 4B shows a cut-away view of the cutting blade 320 mounting relative to the bearing block 330. In the position shown in FIGS. 4A and 4B, the eccentrically mounted cutting blade 320 reaches peak extension as limited by the degree of eccentricity. In this position, the maximum depth of a cut 410 is regulated and the exposed edge of cutting blade 320 is moving at maximum velocity relative to the bearing block, as the blade is rotated as shown by arrow 420 in FIG. 4B.

By continued rotation of the eccentrically mounted cutting blade 320, the cutting blade 320 returns to the safe or parked state as described above. In an aspect of the invention implemented in some embodiments, the cutting blade is caused to automatically return to the parked position when the clinician or other user turns off the device by de-actuating the on/off switch, such as depressing the activation switch, or other actuator.

As noted previously, the exact cutting motion may vary depending on the particular implementation and may, for example, comprise multiple uninterrupted rotations with the cutting blade starting and ending in the safe position or, as a further alternative, may comprise reciprocal rotation about the pivot as a means of cutting tissue.

FIGS. 5A and 5B show an alternative configuration of the eccentrically mounted circular cutting blade 320, according to a further embodiment of the invention. In FIG. 5A, the blade 320 is shown exposed to its full extent. The axle 350 is positioned further from the tip of the bearing block 330, compared with the configuration shown in FIGS. 4A and 4B. Therefore less of the cutting blade 320 is exposed during rotation of the blade. Furthermore, in FIG. 5B the position of axle 350 is rotated from its position in FIG. 4B, resulting in a different blade profile being exposed beyond the bearing block as the blade is rotated.

Figure 6A:
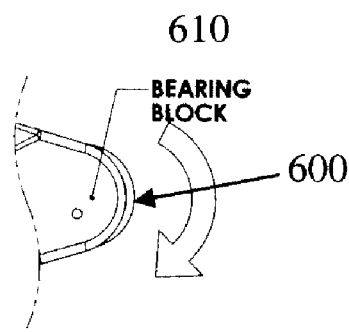
FIGS. 6A-6D illustrate a further alternative range of motion for a cutting assembly in accordance with the invention.
Figure 6B:
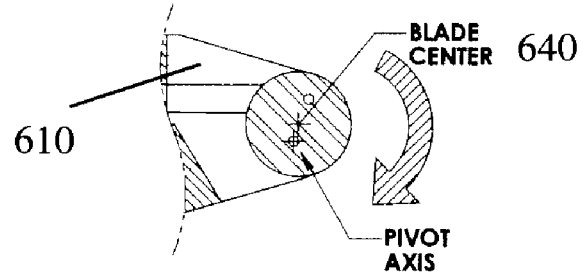
Figure 6C:
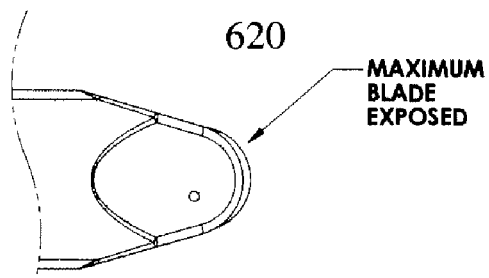
Figure 6D:
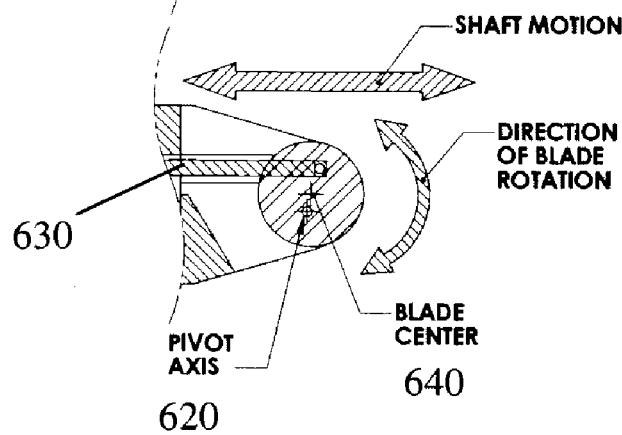
Figure 8A:
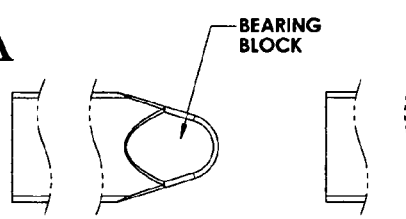
FIGS. 8A-8D illustrate various details of a cutting assembly having an elliptical style blade.
Figure 8B:
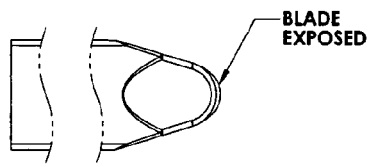
Figure 8C:
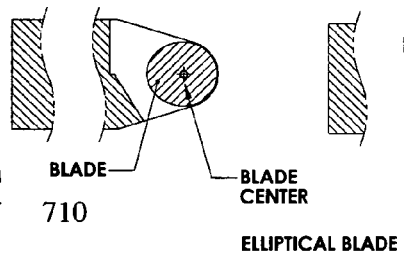
Figure 8D:
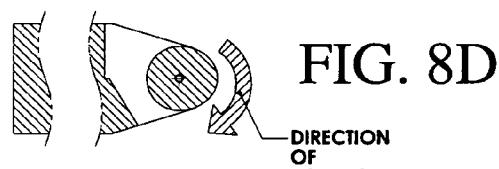

Referring next to FIGS. 6A-6D, an embodiment wherein a blade 600 that is capable of reciprocating motion is shown, where FIG. 6A is a side elevation view of a bearing block 610 and the blade 600, FIG. 6B shows one exemplary rotation about a bearing or pivot 620, FIG. 6C shows the blade at maximum exposure, and FIG. 6D is a cut-away view showing a drive shaft 630 affixed to the blade 600 to cause the reciprocating motion about the pivot 620. Again the amount of blade exposed is determined by the degree of eccentricity in the mounting, or the position of the pivot 620 relative to the blade center 640.

In another alternative implementation, shown in FIGS. 7A-7D, a housing 700 shown in side elevation view in FIGS. 7A and 7B and cut-away side views in FIGS. 7C and 7D a concentrically mounted cutting blade 710 having at least one protruding or "shark-fin" style blade element 720 is intermittently or continuously rotated a fractional revolution, a complete revolution or a multiplicity of revolutions as a means of cutting tissue. As shown in FIG. 7B, the cutting blade 710 is contained within the housing 700 while the blade element 720 is exposed. The blade element 720 may be constructed in a manner to provide a cam like cutting edge with increasing blade engagement as the blade element 720 advances, until the blade element 720 reaches maximum exposure and the exposed edge of the blade reaches maximum velocity relative to the bearing block, as the blade is rotated as indicated by arrow 730 in FIG. 7D.

As an alternative to the "shark-fin" style blade element 720, the cutting blade 710 may have an elliptical shape as shown in FIGS. 8A-8D or any other non-circular shape, including rectangular, triangular, trapezoidal, and so on, such that the blade has a tip portion as a cutting surface which serves to intermittently contact the tissue during rotation.

In a still further alternative implementation shown in FIGS. 9A-9D, a concentrically mounted circular blade 900 is intermittently or continuously rotated about a moveable pivot 910 housed within a protective bearing block 920. A clinician initiated cutting event is actuated by means of a driver 930 that causes the blade to rotate about the pivot 910 and simultaneously advances the blade out of the protective bearing block 920.

Alternatively, as shown in FIGS. 10A-10D, a protective bearing block 1000 is configured to retreat relative to a blade 1010 when a driver mechanism 1030 is actuated, thus exposing the blade 1010 to the tissue.

In either case, the blade rotation mechanism will be an independent element (such as a drive shaft with pinion gear, bearing element, and enclosure) that is able to move longitudinally relative to a shaft within a blade protection housing. In such an arrangement, the bearing block and protective housing may be divided, if desired, and either the blade would be moved forward or the housing moved back. Optionally, the blade may be serrated to enhance cutting specific tissues, and a few of the many examples of available blade designs suitable for use with the present invention are shown in FIGS. 11A-11D.

Figure 12A:
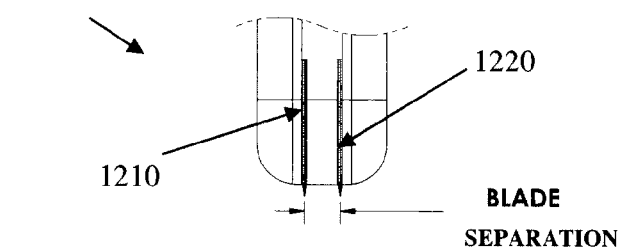
FIGS. 12A-12C illustrate a dual blade configuration.
Figure 12B:
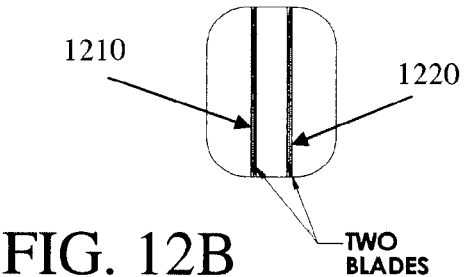
Figure 12C:
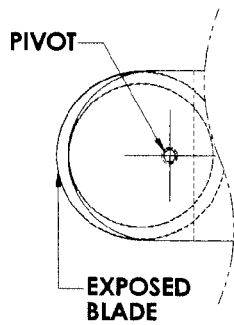

In another implementation shown in FIGS. 12A-12C, more than one blade, such as blades 1210 and 1220, may be utilized. FIG. 12A illustrates in top plan view the cutting assembly 1200. FIG. 12B illustrates a front elevation view of the cutting assembly 1200, including rotary cutting blades 1210 and 1220. FIG. 12C illustrates a side elevation view of the cutting assembly 1200. The blades are mounted parallel to one another and may be used to make parallel incisions or strips of tissues. Furthermore, blades may be mounted so as to move synchronously or asynchronously with respect to the axle; that is, if synchronous, the two blades rotate or advance together, and if asynchronous, the two blades move independently (at different times or rates, for example) relative to one another.

Figure 13A:
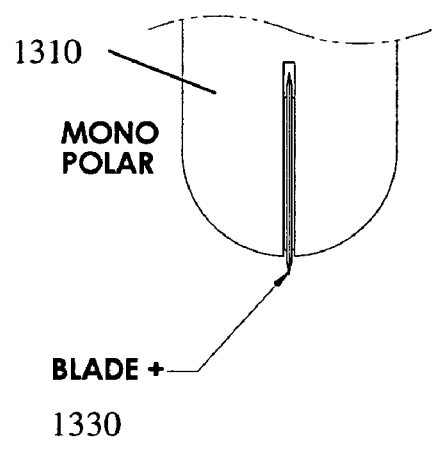
FIGS. 13A-13B illustrate an implementation of a cutting assembly having monopolar and bipolar electrocautery, respectively.
Figure 13B:
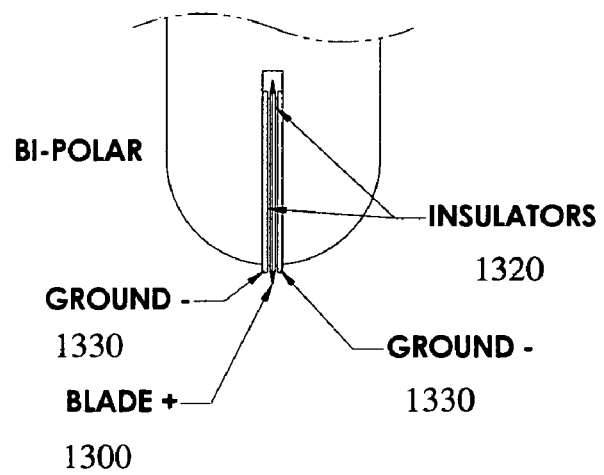

Additionally, as shown in FIGS. 13A-13B, mono-polar or bi-polar electrocautery may be added for further tissue manipulations. Thus, in FIG. 13A, showing a monopolar electrocautery arrangement, a blade 1300 is polarized with a first polarity (for example, positive). Or, as shown in the bipolar arrangement of FIG. 13B, insulators 1320 may be mounted on either side of the blade 1300 and within the housing 1310 such that the blade 1300 has a first polarity and closely juxtaposed contacts 1330 are maintained at the opposite polarity, or at around.

Figure 14:
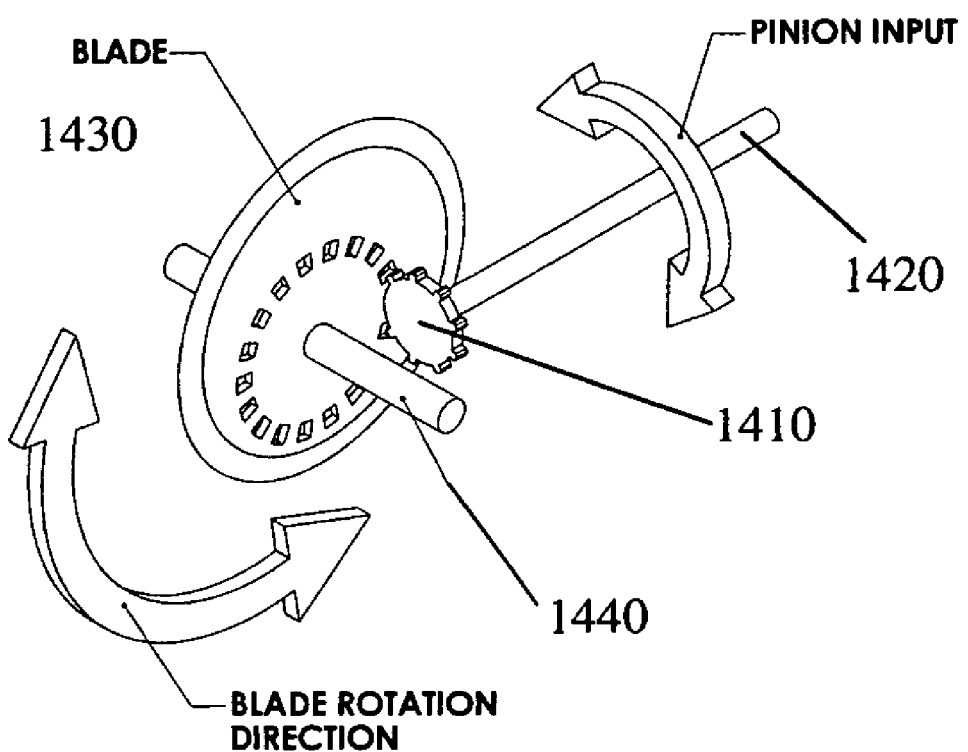
FIG. 14 illustrates a pinion gear drive assembly for actuating the blade.
Figure 15:
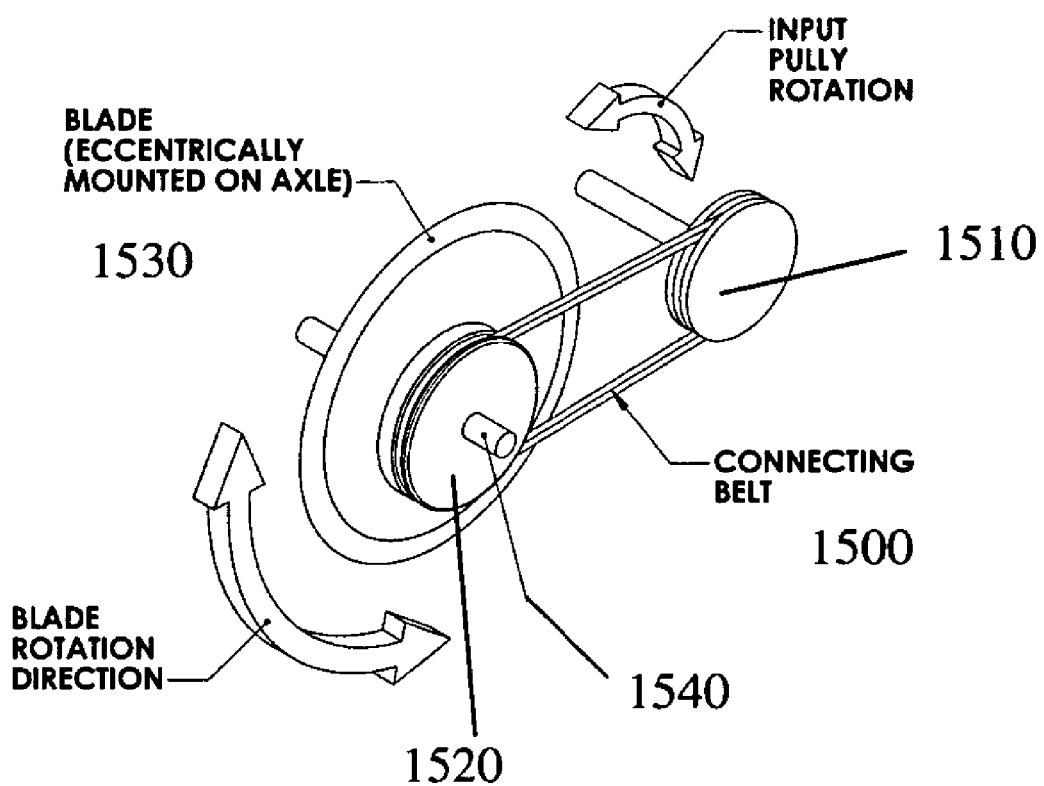
FIG. 15 illustrates a pulley drive assembly for actuating the blade.

Referring next to FIGS. 14-18, many different means of power transmission may be employed to drive the cutting elements. The cutting elements may be driven in a rotary or oscillating mode depending on the clinical application. For example, as shown in FIG. 14, an arrangement of a pinion gear 1410 and shaft 1420 may be used with the blade 1430 notched concentrically about the axle 1440. Or, as shown in FIG. 15, a drive belt, chain or cable 1500 mounted on an input pulley 1510 and a drive pulley 1520 connected to a blade 1530 and an axle 1540 may also be used to transmit power to the blade 1530, where a drive mechanism such as a motor, air turbine or other source of motive force is connected to the axle of the input pulley 1510.

Figure 16:
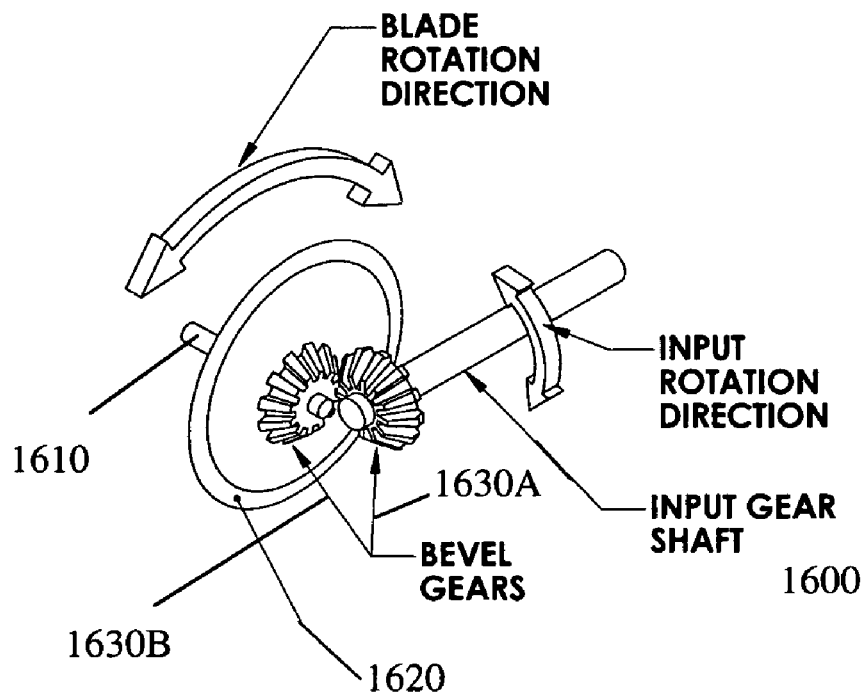
FIG. 16 illustrates a bevel gear drive assembly for actuating the blade.

As shown in FIG. 16, a rotating shaft 1600 mounted perpendicular to an axle 1610 and a blade 1620 may also be used in conjunction with a variety of well known mechanisms such as bevel gears, crown gear sets or spatial revolute-cylindrical-cylindrical-revolute couplings 1630A-B to drive the blade.

Figure 17:
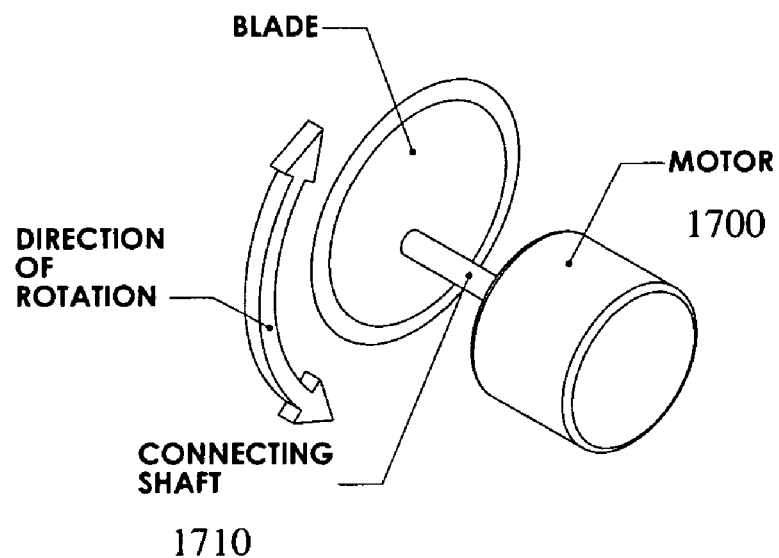
FIG. 17 illustrates a direct motor drive assembly for actuating the blade.
Figure 18:
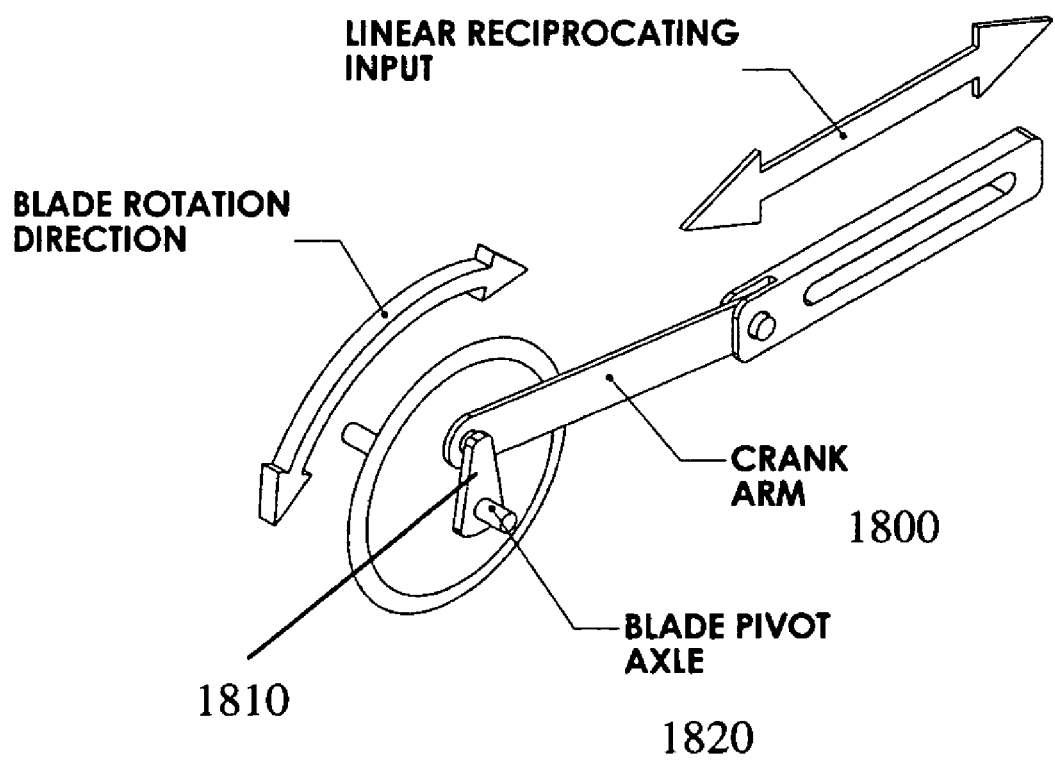
FIG. 18 illustrates a crank arm drive assembly for actuating the blade.

As shown in FIG. 17, a motor 1700 may be directly connected to an axle 1710 and electronically controlled. Or, as shown in FIG. 18, reciprocating motion to a cutting element may also be achieved through the use of a slider crank type mechanism 1800 connected to a cam arm 1810 attached to a blade pivot axle 1820. Alternatively, by mounting the crank 1800 on the outside of the cam arm 1810, full rotation may be achieved. Optionally, the cutting element may also be driven by hydraulic or pneumatic means.

Referring next to FIGS. 19A-19D and FIG. 20, a cutting assembly 1900 is shown having a shaft 1910, a blade 1920, and a housing 1930 with a cavity located at the end of the housing 1930 proximate to the blade 1920. A cantilever spring element 1912 is located at one end of the shaft 1910. The spring element 1912 is located proximate to and in contact with a central axle 1922 of the blade 1920 as shown in FIGS. 19A-D and FIG. 20. The central axle 1922 is positioned within the cavity of the housing 1930, such that the forward motion of the blade 1920, which is caused by the linear motion of the shaft 1910, is limited as seen in the cross-section view of FIG. 19D taken along the line C-C of FIG. 19C. When the central axle 1922 has reached the maximum linear travel in a direction 1950, the blade 1920 is extended the maximum distance out from the housing 1930 as shown in FIG. 19B. However, the shaft 1910 can continue its linear travel in the direction 1950. Accordingly, this linear travel of the shaft 1910 is translated into rotational motion 1960 of the blade 1920 as the shaft 1910 forces a pin 1924, which is secured to the blade 1920, to rotate about the axle 1922 until the spring element 1912 is compressed and the maximum linear motion of the shaft 1910 is reached as shown in FIG. 19C. Consequently, the rotation of the pin 1924 about the axle 1922 results in the rotational motion 1960 of the blade 1920. Thus, the linear motion 1950 of the shaft 1910 first results in extension of the blade 1920 from the housing 1930 and then rotational motion 1960 of the blade 1920 about the axle 1922. FIG. 20 shows a perspective view of the stationary configuration shown in FIG. 19A.

Mounting of the cutting element assembly is generally application specific. However, it is important to note that certain configurations may be useful for multiple applications.

It will thus be appreciated that a new and novel design of incision system has been disclosed. Among the advantages offered by one or more implementations of the invention are a controlled depth of cut, a retractable blade offering increased user and patient safety, high velocity (relative to the prior art) cutting element permitting lower cutting forces to be applied by the user, and flexible mounting arrangements including articulated and more conventional mountings. Having fully disclosed a variety of implementations of the present invention, it will be appreciated by those skilled in the art that numerous alternatives and equivalents exist which do not materially alter the invention described herein. Therefore, the invention is not intended to be limited by the foregoing description, but instead only by the appended claims.

We claim:

1. A system for rapid manipulation and cutting comprising:
   a housing,
   a bearing block attached to an end of the housing,
   a first cutting element, the first cutting element being an eccentric disc rotatably connected to the bearing block by an axle, wherein the first cutting element is configured to rotate eccentrically, and
   a drive mechanism adapted to be mounted at least partly within the housing and operatively connected to the first cutting element for providing torque about the axle of the first cutting element,
   wherein the first cutting element, the axle, the housing and the bearing block are configured such that a cutting edge of the disc is exposed beyond the end of the bearing block distal to the housing for only a part of the eccentric rotation, and the cutting element is exposed beyond the housing for the part of the eccentric rotation.

2. The system of claim 1 wherein the housing is roughly cylindrical, the roughly cylindrical housing having an altitude and a radius, the altitude being much larger than the radius.

3. The system of claim 1 wherein the housing is shaped as a handpiece.

4. The system of claim 1 wherein the housing is shaped for use as a tissue manipulator for blunt force dissection.

5. The system of claim 1, wherein the first cutting element is adapted for cutting tissue.

6. The system of claim 5 wherein the housing is adapted for use as a tissue probe.

7. The system of claim 1, wherein the first cutting element is adapted for cutting man-made materials.

8. The system of claim 1 wherein the system includes means for electrocautery.

9. The system of claim 1 wherein the drive mechanism includes a pinion gear assembly.

10. The system of claim 1 wherein the drive mechanism includes a pulley drive assembly.

11. The system of claim 1 wherein the drive mechanism includes a bevel gear drive assembly.

12. The system of claim 1 wherein the drive mechanism includes a direct motor drive assembly.

13. The system of claim 1 wherein the drive mechanism includes a crank arm drive assembly.

14. The system of claim 1 further comprising a second cutting element.

15. The system of claim 1 wherein the drive mechanism includes hydraulic means.

16. The system of claim 1 wherein the drive mechanism includes pneumatic means.

17. The system of claim 1 wherein the system is configured to provide a variable depth of cut determined by the eccentricity of the first cutting element.

18. The system of claim 1 wherein the system is configured to provide a variable ramp angle of the incision determined by the eccentricity of the first cutting element.

19. The system of claim 1 wherein the system is configured to provide a variable rate of cut determined by the eccentricity of the first cutting element.

20. The system of claim 1 wherein the disc is eccentrically mounted on the axle.

21. The system of claim 1 wherein the disc is circular.

22. The system of claim 1 wherein the disc is elliptical.

23. The system of claim 14, wherein said second cutting element is an eccentric disc rotatably connected to the bearing block by the axle, said second cutting element being configured to rotate eccentrically, and wherein said first cutting element and said second cutting element are parallel.

24. The system of claim 23, wherein the first cutting element and the second cutting element are configured to move synchronously.

* * * * *